United States Patent [19]

Prosl et al.

[11] Patent Number: 5,894,011
[45] Date of Patent: Apr. 13, 1999

[54] FLOW REVERSING DEVICE FOR HEMODIALYSIS

[76] Inventors: Frank R. Prosl, 474 Franklin St., Duxbury, Mass. 02372; Joseph Megerman, 70 Williston Rd., Brookline, Mass. 02146; Brian K. Estabrook, 24 West St., Foxboro, Mass. 02035

[21] Appl. No.: 09/104,310

[22] Filed: Jun. 24, 1998

[51] Int. Cl.⁶ .................. A61M 1/14; A61M 37/00; F25B 13/00; B01D 11/00
[52] U.S. Cl. .................. 422/44; 604/4; 604/5; 210/636; 210/321.72; 210/646; 60/454; 62/160; 62/324.1
[58] Field of Search .................. 422/44; 604/5, 604/4; 62/324.1, 160; 60/454, 329; 119/14.01

[56] References Cited

U.S. PATENT DOCUMENTS

| | | | |
|---|---|---|---|
| 3,906,574 | 9/1975 | Kaeser | 15/29 |
| 4,009,572 | 3/1977 | Cer | 60/454 |
| 4,324,662 | 4/1982 | Schnell | 210/646 |
| 4,439,984 | 4/1984 | Martin | 60/454 |
| 4,475,332 | 10/1984 | Anderson et al. | 60/329 |
| 4,573,492 | 3/1986 | White | 62/324.1 |
| 4,619,639 | 10/1986 | Nose et al. | 604/6 |
| 4,766,734 | 8/1988 | Dudley | 62/160 |
| 4,885,087 | 12/1989 | Kopf | 210/321.72 |
| 5,120,303 | 6/1992 | Hombrouckx | 604/4 |
| 5,492,090 | 2/1996 | Bucker | 119/14.01 |
| 5,605,630 | 2/1997 | Shibata | 210/646 |
| 5,650,071 | 7/1997 | Brugger et al. | 210/646 |
| 5,690,829 | 11/1997 | Lauer | 210/636 |
| 5,720,716 | 2/1998 | Blakeslee et al. | 604/4 |

Primary Examiner—John G. Weiss
Assistant Examiner—Cheryl L. Huseman

[57] ABSTRACT

A device for selectively controlling the direction of blood flow to and from the patient during hemodialysis comprises two interlocking disks that rotate in relation to each other without separating. The two disks have fluid fittings that allow the blood lines attached to the patient to connect to one of the disks and the blood inlet and outlet for the hemodialysis machine to connect to the other. The center of each fluid fitting is a channel that aligns to a corresponding channel in the other disk. The disks rotate between two fixed relative positions, referred to herein as preferred alignments. The preferred alignments are such that the line drawing blood from the patient in the first preferred alignment becomes the line returning blood to the patient in the second preferred alignment, and the line returning blood to the patient in the first preferred alignment becomes the line drawing blood from the patient in the second preferred alignment. A bypass channel allows blood to flow from the outlet to the inlet of the hemodialysis machine when the device is in neither of its two preferred alignments.

6 Claims, 2 Drawing Sheets

FLOW REVERSING DEVICE FOR HEMODIALYSIS

FIELD OF THE INVENTION

This invention relates to systems for replacement of kidney function in patients with end stage renal disease (ESRD), and more particularly to the treatment of ESRD by means of hemodialysis. In hemodialysis systems, the current invention relates to an apparatus for selectively controlling the direction of flow in a portion of the blood circuit of a patient undergoing hemodialysis. Specifically, in the blood circuit comprising the closed loop through the patient's vascular system and through the hemodialysis machine, this invention relates to changing the direction of flow on the patient side only, that is, to and from the patient's vascular system, without altering flow through the hemodialysis apparatus. The current invention further relates to shunting the flow of fluid in the hemodialysis machine during the flow reversal transition so that flow through the machine itself can continue unabated during switching.

BACKGROUND OF THE INVENTION

In present day medical practice, hemodialysis is the standard therapy for treating ESRD. This therapy involves dialyzing the patient's blood several times a week. During treatment, the patient's vascular system is connected to a hemodialysis machine for sessions lasting several hours. This connection forms a blood circuit whereby blood is drawn from the patient through a needle connected to a flexible blood line, cycled through a hemodialysis machine that removes waste products including water, urea, and other impurities from the blood, and returned to the patient via a second blood line and needle. As used herein, reversing the direction of flow in the blood circuit means drawing blood through the needle which had previously been used to return blood to the patient and returning blood through the needle which had previously been used to draw blood from the patient without changing the direction that blood circulates through the hemodialysis machine. This change is also referred to herein as flow reversal or flow reversal in the patient portion of the blood circuit.

Traditionally, access to the patient's blood stream has been provided by an arterio/venous ("A/V") fistula or by a polytetrafluoroethylene ("PTFE") graft. An A/V fistula is a surgical construct joining an artery to a vein. The shunting of blood from an artery to a vein increases pressure on the vein, which pressure enlarges its diameter and thickens its walls. A fully developed fistula can be punctured with needles to access the patient's blood system. A PTFE graft is an artificial blood vessel used to connect the artery to the vein. The material used for the graft is suitable for puncturing with needles to achieve the necessary access to the patient's blood system. A third method of obtaining access for hemodialysis is to use percutaneous catheters which allow blood to be withdrawn from one lumen and returned by a second lumen. New methods of accessing the patient's blood stream are also being developed. The Dialock™ system accesses the superior vena cava through one or more catheters connected to an implanted prosthesis. Needles are inserted into the prosthesis to effect access to the patient's blood stream.

It is advantageous to operate hemodialysis therapy with blood flows at the highest rates possible while avoiding damage to the blood cells. The device facilitates selection of the best flow path at each dialysis session giving the highest flow rate for the maximum allowed negative pressure.

One of the difficulties that can arise in chronic hemodialysis is maintaining adequate blood flow during treatment sessions. When flow rates decrease significantly during a session, the attendant could in many cases restore adequate flow by switching the blood lines. In current practice, the attendant must usually turn off the hemodialysis machine. This process lengthens the dialysis session while the machine is primed and restarted. In addition, switching the blood lines involves disconnecting the lines, which can cause bleeding and allow air to enter the lines.

Disconnecting the lines also breaks the microbe barrier, increasing the possibility of infection. Thus, blood lines are typically not switched during hemodialysis treatment absent extreme need, despite therapeutic benefits that could accrue from periodically reversing the direction of flow in the patient portion of the blood circuit. If flow direction could be reversed easily during operation, then the best path, the one which yields lowest negative pressure reading, could be easily selected and reselected as the session proceeds.

A further situation which often arises is that the flow resistance in each of the catheters in the patient is different. The pressure drop or resistance that blood cells can be subjected to without damage is higher when the blood is at pressures greater than atmospheric (return side of the dialysis machine) than when the cellular components of blood are subjected to negative pressures. Absence of ability to reverse the direction of blood flow easily can result in lower flow rates, larger negative pressures, and increased possibility of damage to blood cells.

Another difficulty that often arises with chronic hemodialysis is the possibility that the patient will develop a thrombus or blood clot that partially or wholly occludes a vascular access created by a fistula or vascular graft. When a fistula or graft becomes blocked, surgery is frequently needed to restore the venous access to a useful condition or replace the access site. A balloon angioplasty may be used to enlarge the lumen of the fistula or graft and prevent the immediate formation of thrombosis, thereby extending the life of the access. When a site can no longer be restored, it must be replaced. Replacing an access is a serious matter because patients have only a limited number of access sites for A/V fistulas and PTFE grafts.

Even when dialysis is being performed using catheters or Dialock™, flow can become impaired. Flow impairment often occurs because of the formation of a fibrin sheath or a clot at the tip of a catheter lumen. In some instances, this sheath or clot can completely block flow if the catheter lumen is being used for withdrawing blood from the patient. (A clot at the tip of a catheter lumen usually does not interfere with blood return.) In many cases, therefore, the impairment could be corrected or mitigated by reversing the direction of blood flow during a dialysis. Moreover, maintaining a high rate of blood flow throughout the session slows the development of thrombi and potentially prolongs the useful life of the access. Furthermore, there is a possibility that reversing flow direction during a hemodialysis session or between successive sessions will reduce the occurrence of fibrin sheath formation.

It is known to use spool valves or three-way valves with syringes, and it has been suggested that these types of valves could accomplish flow reversal. However, these valves were not intended to accommodate high rates of blood flow. Specifically, the fluid flowing through valves of these types is required to make abrupt turns, creating turbulence in the blood flow. These valves also contain abrupt enlargements and restrictions which also engender turbulent flow. Turbulence reduces the blood flow rate and promotes the formation of thrombi. These valves have the additional prohibition that they contain spaces that could accumulate stagnant blood.

A number of inventions relate to reversing the direction of flow in connection with hemodialysis. U.S. Pat. No. 5,605,630 discloses, in pertinent part, a "blood flow direction changeover means that is attached to the blood circuit for changing over the direction of the blood flow through the dialyzer from one direction to the other." Similarly, U.S. Pat. No. 4,885,087 concerns the means of changing the directional flow through a mass transfer chamber such as a hemodialysis machine. U.S. Pat. No. 4,324,662 describes a "flow reversing valve system . . . positioned in the flow system for cooperation with the dialyzer to selectively control the direction of dialysis solution flow within the dialyzer in either a first direction or a second reverse direction." Each of these inventions concerns reversing or alternating flow into a transfer chamber such as a dialyzer. The inventions are unsuited to changing the flow of blood to and from the patient, because they are not concerned with maintaining laminar flow in the blood circuit. Even if these inventions were adapted to reverse the direction of flow in the patient portion of the blood circuit, none teaches a bypass function to ensure that the dialysis machine can continue to operate while the direction of blood in the lines is being reversed.

Several other inventions relate peripherally to the subject matter of the instant invention. U.S. Pat. No. 4,586,920 discloses an inflow/outflow directional valve acting in combination with a bypass valve used in a continuous flow peritoneal dialysis system. However, the so-called directional valve does not change the direction of flow through the peritoneal catheters—the inlet and outlet catheters remain distinct during dialysis. U.S. Pat. No. 4,898,669 describes a rotating valve employed in vascular access having two positions: the first connecting the blood system inflow and outflow with two external ports and the second position acting as a bypass to short circuit blood system inflow and outflow, and to allow flushing of the external ports. This device does not teach reversing flow in the patient portion of the blood circuit, particularly as it might be combined with its bypass function.

A number of inventions manipulate the passage of blood through valves and manifolds. U.S. Pat. No. 4,946,434 "provides a plurality of sterile paths for directing the flow of fluids." Similarly, U.S. Pat. No. 4,821,996 discloses a "multi-position rotary valve system usable with a disposable fluid transfer set . . ." These and other similar inventions rely on clamping to selectively open and shut flow paths. Clamping is unsuitable in the current circumstances because of the need to maintain blood flow through the hemodialysis machine during flow reversal operations. Any device which necessitates restarting the hemodialysis machine would not be useful for routinely reversing flow in the patient portion of the blood circuit.

Accordingly, an object of this invention is to provide for the easy and convenient selection of which needle or catheter will be used to draw blood and which will be used to return blood at any particular time during hemodialysis treatment sessions. Another object of this invention is to have a device that is compatible with high rates of flow in dialysis methods such as Dialock™ which utilize catheters. Yet another object of this invention is to accomplish the flow reversal function while minimizing the amount of turbulence associated with blood flow through the device. Still another object of the invention is to provide a device that is safe to use. A further object of the invention is to minimize stagnant flow regions in the device. Still another object of this invention is to provide a device that is easily added to existing hemodialysis set ups and treatment programs. Still another object of this invention is to provide a low cost, easily manufactured, sterile disposable device compatible with the rest of the blood circuit.

SUMMARY OF THE INVENTION

The present invention is a device for reversing the direction of flow to and from the patient without interrupting or changing the direction of flow through the portion of the blood circuit which passes through the blood treatment apparatus, comprising: a first patient fluid fitting and a second patient fluid fitting each of which is able to provide flow in either direction with respect to the patient; a first blood treatment apparatus fluid fitting which establishes fluid flow to the blood treatment apparatus and a second blood treatment apparatus fluid fitting which establishes fluid flow from the blood treatment apparatus; a mechanism having a plurality of positions, said plurality comprising at least a first position that simultaneously aligns the first patient fluid fitting with the first blood treatment apparatus fluid fitting and the second patient fluid fitting with the second blood treatment apparatus fluid fitting, and a second position that simultaneously aligns the first patient fluid fitting with the second blood treatment apparatus fluid fitting and the second patient fluid fitting with the first blood treatment apparatus fluid fitting and, while in said first position and said second position, said mechanism maintaining substantially unobstructed fluid connections between aligned fluid fittings; and a fluid conduit which maintains substantially unobstructed fluid connection between the first blood treatment apparatus fluid fitting and the second blood treatment apparatus fluid fitting in all of the plurality of positions other than the first position and the second position and which in all of the plurality of positions simultaneously prevents flow to or from the first patient fluid fitting and the second patient fluid fitting.

More particularly, this invention is a device for reversing the direction of flow to and from the patient without interrupting or changing the direction of flow through the portion of the blood circuit which passes through the blood treatment apparatus, comprising: a first side for connection with a patient and a second side for connection with an external blood treatment apparatus; on the first side, two patient fluid fittings each of which is able to provide flow either to or from the patient; on the second side, a first blood treatment apparatus fluid fitting which establishes fluid flow to the blood treatment apparatus and a second blood treatment apparatus fluid fitting which establishes fluid flow from the blood treatment apparatus; said first side and said second side being configured to enable assembly into a unit substantially free of leaks with said blood treatment apparatus fluid fittings and said patient fluid fittings being external to the assembly and such that the surfaces of the two sides inside the assembly are able to move slidably in relation to one another so as to form at least two relative orientations of the two sides; said first side and said second side being further so shaped that the assembly establishes between the two sides a plurality of passageways which establish variable fluid communication with other cavities depending on the relative orientation of the two sides, the first of said at least two relative orientations of the sides being such that the first blood treatment apparatus fluid fitting is substantially coaxial with the first patient fluid fitting on the patient side and simultaneously the second blood treatment fluid fitting is substantially coaxial with the second patient fluid fitting on the patient side, so as to create two substantially straight through passageways for the passage of the patient's blood to and from the blood treatment apparatus; the second of said at least two relative orientations of the sides being such that the first blood treatment apparatus fluid fitting is substantially coaxial with the second patient fluid fitting on the patient side and simultaneously the second blood treatment fluid fitting is substantially coaxial with the first patient fluid fitting on the patient side, so as to create two substantially straight through passageways for the passage of the patient's blood to and from the blood treatment apparatus which are different from those in the first relative orientation; and at least one of the assemblies' plurality of passageways which establish variable fluid communication with other cavities depending on the relative orientation of the two sides being so configured as to create an unobstructed fluid path from the first blood treatment apparatus fluid fitting to the second blood treatment apparatus fluid fitting such that flow through the blood treatment portion of the entire blood circuit is uninterrupted during a transition from a first of the at least two relative orientations of the two sides to a second of the at least two relative orientations of the two sides and in all of the at least two relative orientations other than the first and second and simultaneously fluid flow between the two patient fluid fittings is prevented in all of the at least two relative orientations.

The invention thus provides a means of reversing the direction of flow in the patient portion of the blood circuit. This reversal can be accomplished easily without disconnecting the lines during treatment and without shutting off and restarting the dialysis machine. Flow through the dialysis machine continues uninterrupted during switching. Further, this invention can be fabricated to comprise a low cost sterile disposable unit that, in its preferred embodiment, consists essentially of two pieces of molded plastic snapped and preferably locked together with selective heat shrinking. The present invention also enables the user to choose an inlet/outlet configuration that minimizes the pressure differential, thereby maximizing flow through the dialysis machine.

Minimizing the amount of turbulence associated with blood flow through the device is accomplished by ensuring that channels are aligned, without sharp bends or turns, and sized to be compatible with the inner cross section of the blood lines. The device avoids clotting and/or stagnation of blood flow because it contains no sharp turns or changes in diameter in the fluid fittings, thereby promoting laminar flow. The design provides for any clots or stagnant blood occurring while the device is operating in its bypass mode to be flushed through (and removed by) the dialysis machine.

The invention also promotes safety in use in a number of ways. First, the design configuration is very simple and suitable for mass production as a sterile disposable, thereby minimizing the possibility of infection from using the device. Second, it is not complicated to operate and the failsafe design minimizes the possibility of user error. Third, the invention allows flow to be reversed manually by a single twisting motion without requiring the application of undue force or mechanical assistance. Fourth, the invention maintains the sterile conditions in the entire blood circuit during the flow reversal operation. The invention does not allow air to enter the blood circuit or blood to be lost during flow reversal. Fifth, since flow in the blood lines may be reversed easily within a cycle, it eliminates or reduces the need to rely on maintaining accurate records, and reduces the possibility that inaccuracy or confusion in interpreting the records will lead to suboptimal treatment.

The invention increases functionality of the blood line by allowing for blood flow to and from the patient to be shut off. This allows the blood lines to be disconnected from the needles during a hemodialysis session or the needle placement to be revised while preventing the loss of blood from the blood line and preventing air from entering the blood circuit.

The device as designed is compatible with a conventional blood access circuit or easily added as an ancillary device for use with a prosthesis such as Dialock™. It is inexpensive to manufacture so it can be used as a sterile disposable, eliminating the need to sterilize the device after use.

DESCRIPTION OF THE PREFERRED EMBODIMENT

Figure 1:
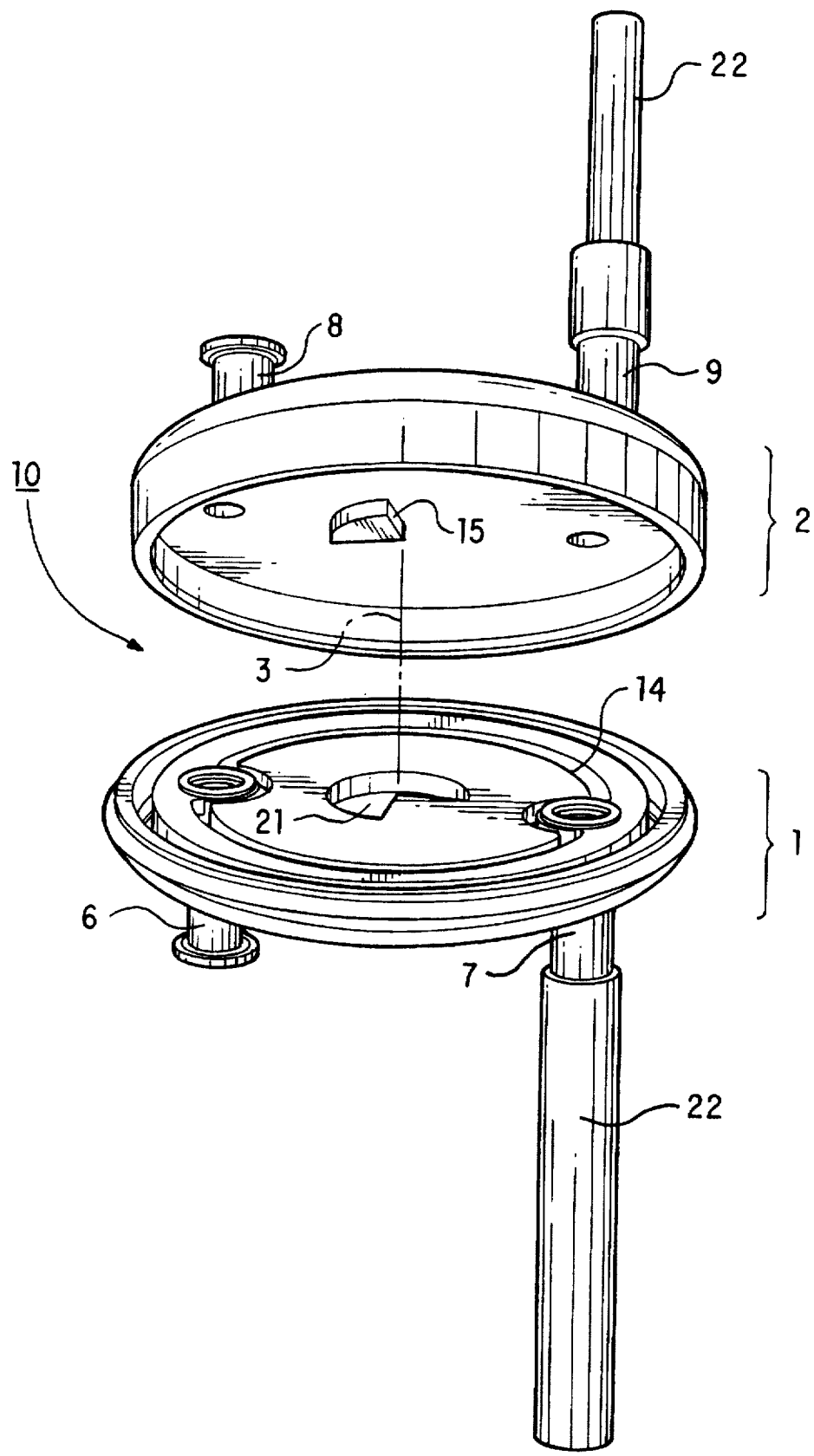
FIG. 1 sets forth an expanded isometric view of the flow reversal valve arrangement.
Figures 2, 3:
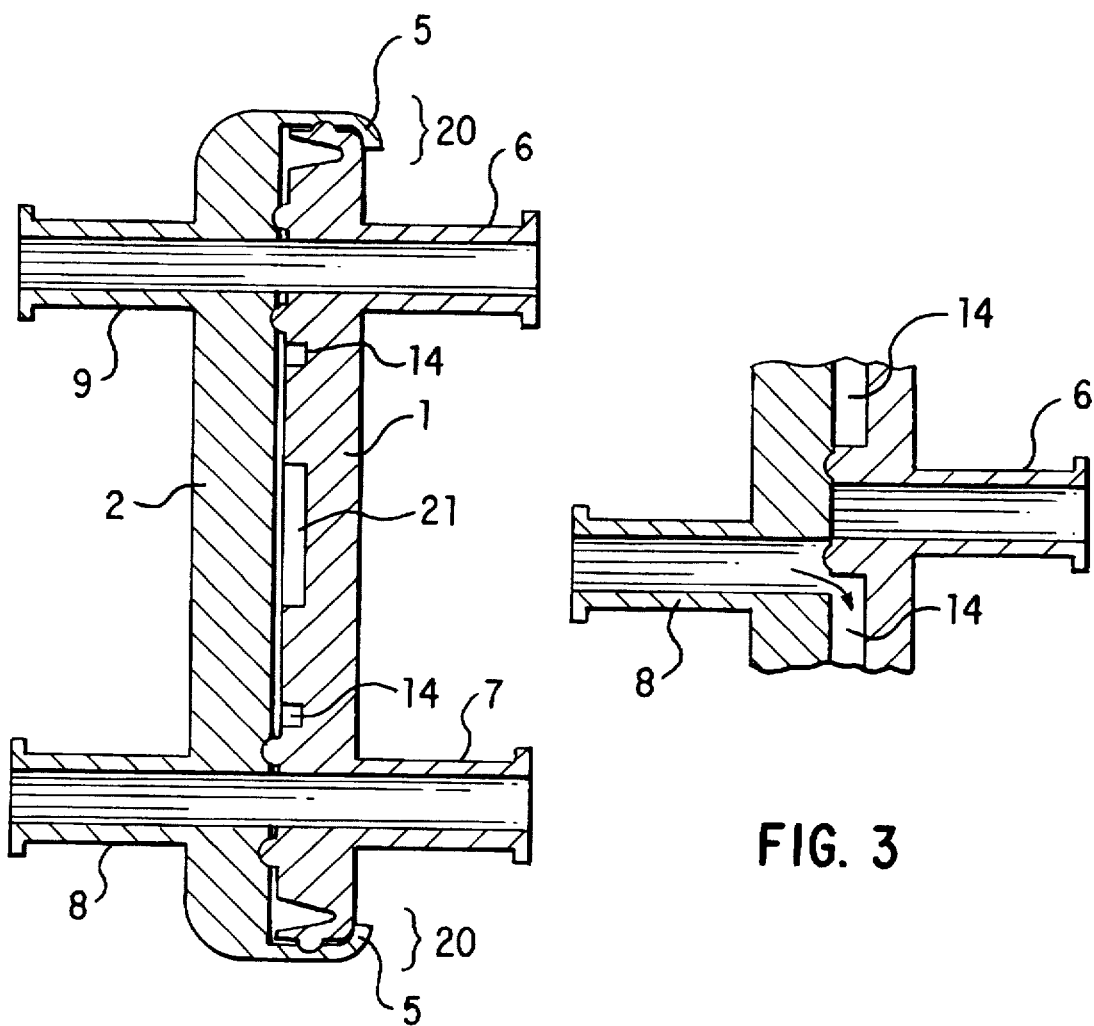
FIG. 2 shows a cross sectional view of the interlocking disk arrangement comprising the flow reversal valve with the alignment set for normal flow to and from the patient.
FIG. 3 is a partial cross sectional view of the flow reversing valve in the intermediate position in which blood does not flow into or out of the patient but is shunted to preclude having to shut down the hemodialysis machine.

As shown in FIG. 1, the device 10 comprises two interlocking disks 1 and 2. The disks may be made of any bio-compatible material with sufficient rigidity to maintain the shape of the disk structure, preferably either plastic or metal. Although referred to herein as disks, these devices need not be circular. They may be oval, octagonal, or some other shape for ergonomic or manufacturing purposes. Interlocking of the disks may be accomplished in a number of different ways that allow the disks to rotate relative to each other without separating. For example, as further shown in FIGS. 1 and 2, the disks can be snapped, molded, or formed together such that a tight joint is maintained between disks 1 and 2. In the preferred embodiment shown in FIG. 2, disks 1 and 2 are circular and are joined at their periphery 20. Peripheral joining can be effected by addition of a lip 5 that rides in a groove around the periphery of both disks, as shown in FIG. 2. Such lip 5 may be formed of metal, plastic, or an equivalent so long as it is capable of maintaining a tight joint between disks 1 and 2 to preclude separation. In the preferred embodiment, lip 5 is integrally molded into the periphery of disks 1 and 2 during molding of the disks themselves rather than being a separate lip component that effects interlocking, as shown in FIG. 2. In the preferred embodiment, disks 1 and 2 snap together and are held in place by lip 5 to effect a tight joint. Alternatively, lip 5 can be fabricated from a cylindrical procession by a process such as selective heat shrinking after insertion of the second disk. In a further alternative, a tight joint between disks 1 and 2 may be effected by attaching the disks along their centerline 3, shown in FIG. 1, using a bolt or rivet of metal, formed plastic or equivalent material (not shown). Note also that the disks may be interlocked by using a combination of the above methods. For example, they may be joined during manufacturing at both centerline 3 and periphery 20.

Choice of materials for disks 1 and 2 will dictate the preferred means of interlocking the disks. Factors that will effect selection of the preferred joining means include the brittleness or ductility of the plastic used for the disk, the rigidity of the disk structure to deformation and the pressure that the joint(s) must withstand to prevent the seepage of blood or reduce seepage to acceptable levels. Note that if gaskets are used, the amount of seepage will also be a function of the gasket's materials, sizes and locations.

As shown in FIGS. 1 and 2, each disk has two fluid fittings. Fluid fittings 6 and 7 on disk 1 are used to connect the device to blood lines running to the patient. As shown in FIGS. 1, 2, and 3, fluid fittings 8 and 9 on disk 2 are used to connect the device to blood lines running to the inlet and outlet of the hemodialysis machine. A variety of designs are possible for the fluid fittings. Connection may be maintained by easing the blood line flexible tubing 22 over a lip such that the connection is maintained by contraction of the blood line, as illustrated in FIG. 1. Alternatively, blood lines may be clamped to the fluid fittings. In the preferred embodiment, the inner diameter of each fluid fitting is the same as the inner diameter of the blood lines in order to maintain laminar flow in the transition between the device and the blood line insofar as possible.

As shown in FIGS. 1, 2, and 3, fluid fittings 6 through 9 may be integrally molded as part of disks 1 and 2. Alternatively, they may be separate pieces fastened to the disks. Accordingly, they may be metal, plastic, or other suitable material.

The preferred embodiment is a single-use device. Accordingly, the most cost-effective and simplest device would appear to be disks with embedded fluid fittings joined during manufacturing by interlocking the disk structures themselves either at the hub, the periphery or both. If the choice of plastics for the disk indicated that additional strength would be needed, or alignment or ease of operation became a concern, a hub or periphery attachment might be formed separately. Note that prototypes for testing might be interlocked differently than production units because of constraints on machining or manufacturing small lot sizes.

If gaskets are required to prevent or limit the seepage of blood during hemodialysis, such gaskets would be inserted approximately at the location where the base of each fluid fitting intersects the inner surface of the disk (not shown). Alternatively, gaskets could be fitted only to the patient-side fluid fittings 6 and 7 leaving hemodialysis machine-side fluid fittings 8 and 9 without gaskets. The gaskets may be formed of flexible (compressible) plastic or rubber.

The disks have two preferred alignments. The first preferred alignment, shown in FIG. 1, has the centerline of fluid fitting 6 aligned with the centerline of fluid fitting 8 and the centerline of fluid fitting 7 aligned with the centerline of fluid fitting 9. The second preferred alignment, shown in FIG. 2, has the centerline of fluid fitting 6 aligned with the centerline of fluid fitting 9 and the centerline of fluid fitting 7 aligned with the centerline of fluid fitting 8. In the preferred embodiment the relative location of the fluid fittings and their positions on the faces of disks 1 and 2 have been chosen to avoid any abrupt turns in order to be compatible with high flow rates, and for ease of manufacture. Other configurations are possible but less desirable. Disks 1 and 2 may be marked to show when each of the preferred alignments has been achieved. In the preferred embodiment, tooth 15 projecting into a compatibly-sized cavity 21 surrounding centerline 3, shown in FIG. 1, provides a mechanical indication that the relative position of the two disks is a preferred alignment. In the preferred embodiment, reversing flow involves rotating the two disks such that tooth 15 travels the length of cavity 21 and fluid fittings 6, 7, 8, and 9 alternate between their two preferred alignments.

In addition to resting in either of the two preferred alignments, the disks are free to rotate to and rest in a range of intermediate relative positions. When the relative orientation of disks 1 and 2 is not in either of the preferred alignments, as shown in FIG. 3, a channel 14 in disk 1 (patient-side disk) allows blood to flow between fluid fittings 8 and 9. This permits the hemodialysis machine to continue to operate even though fluid fittings 6 and 7 are blocked so no blood is being drawn from or returned to the patient. This is the bypass mode of operation. The device being operated in the bypass mode acts as a shut-off and allows a variety of activities to be accomplished, such as repositioning a needle, without shutting off the hemodialysis machine.

The primary function of channel 14 is to facilitate the transition from one preferred alignment to the other thereby reversing flow in the patient blood lines without disconnecting them or shutting off the hemodialysis machine. Channel 14 may be in any shape or form or may be simply an open area in disk 1 that allows blood to flow between fluid fittings 8 and 9. In a preferred embodiment, however, channel 14 is of the same cross-sectional area as the blood lines and the inner diameter of fluid fittings 6 through 9. In another embodiment, channel 14 may be somewhat smaller to simulate the pressure head when the patient is connected to the device.

Note that any clotting or stagnant blood in the channel will be circulated to and filtered by the hemodialysis machine and will not be able to pass into the patient's blood. Optionally, in another embodiment (not shown), gaskets on either side of channel 14 may be used to prevent or reduce blood seepage from channel 14, depending on the tightness of fit between the two disks.

In yet another embodiment, pressure gages (not shown) may be located on the inlet and outlet to the hemodialysis machine respectively to measure the pressure differential between the two lines and provide a signal that can be used to decide when to activate the flow reversal function.

We claim:

1. In a system for administering extra-corporeal therapy to blood comprising a blood circuit connecting a blood treatment apparatus such as a hemodialysis machine to a patient's vascular system, a device for reversing the direction of flow to and from the patient without interrupting or changing the direction of flow through the portion of the blood circuit which passes through the blood treatment apparatus, said device comprising:

a. a first patient fluid fitting and a second patient fluid fitting each of which is able to provide flow in either direction with respect to the patient;

b. a first blood treatment apparatus fluid fitting which establishes fluid flow to the blood treatment apparatus and a second blood treatment apparatus fluid fitting which establishes fluid flow from the blood treatment apparatus;

c. a mechanism having a plurality of positions, said plurality comprising at least a first position that simultaneously aligns the first patient fluid fitting with the first blood treatment apparatus fluid fitting and the second patient fluid fitting with the second blood treatment apparatus fluid fitting, and a second position that simultaneously aligns the first patient fluid fitting with the second blood treatment apparatus fluid fitting and the second patient fluid fitting with the first blood treatment apparatus fluid fitting and, while in said first position and said second position, said mechanism maintaining substantially unobstructed fluid connections between aligned fluid fittings; and d. a fluid conduit which maintains substantially unobstructed fluid connection between the first blood treatment apparatus fluid fitting and the second blood treatment apparatus fluid fitting in all of the plurality of positions other than the first position and the second position and which in all of the plurality of positions simultaneously prevents flow to or from the first patient fluid fitting and the second patient fluid fitting.

2. The device of claim 1 in which the fluid conduit is a channel within the device along which said blood treatment apparatus fluid fittings move.

3. The device of claim 1 in which the device comprises an assembly of a first side and a second side, the first side containing the first and second patient fluid fittings and the second side containing the first and second blood treatment apparatus fluid fittings.

4. The device of claim 3 in which the assembly of the first side and the second side creates the mechanism for establishing the plurality of positions.

5. The device of claim 3 in which the assembly of the first side and the second side creates the fluid conduit by establishing a movable channel internal to the assembly.

6. In a system for administering extra-corporeal therapy to blood comprising a blood circuit connecting a blood treatment apparatus such as a hemodialysis machine to a patient's vascular system, a device for reversing the direction of flow to and from the patient without interrupting or changing the direction of flow through the portion of the blood circuit which passes through the blood treatment apparatus, said device comprising:

a. a first side for connection with a patient and a second side for connection with an external blood treatment apparatus;

b. on the first side, two patient fluid fittings each of which is able to provide flow either to or from the patient;

c. on the second side, a first blood treatment apparatus fluid fitting which establishes fluid flow to the blood treatment apparatus and a second blood treatment apparatus fluid fitting which establishes fluid flow from the blood treatment apparatus;

d. said first side and said second side being configured to enable assembly into a unit substantially free of leaks with said blood treatment apparatus fluid fittings and said patient fluid fittings being external to the assembly and such that the surfaces of the two sides inside the assembly are able to move slidably in relation to one another so as to form at least two relative orientations of the two sides;

e. said first side and said second side being further so shaped that the assembly establishes between the two sides a plurality of passageways which establish variable fluid communication with other cavities depending on the relative orientation of the two sides;

f. the first of said at least two relative orientations of the sides being such that the first blood treatment apparatus fluid fitting is substantially coaxial with the first patient fluid fitting on the patient side and simultaneously the second blood treatment fluid fitting is substantially coaxial with the second patient fluid fitting on the patient side, so as to create two substantially straight through passageways for the passage of the patient's blood to and from the blood treatment apparatus;

g. the second of said at least two relative orientations of the sides being such that the first blood treatment apparatus fluid fitting is substantially coaxial with the second patient fluid fitting on the patient side and simultaneously the second blood treatment fluid fitting is substantially coaxial with the first patient fluid fitting on the patient side, so as to create two substantially straight through passageways for the passage of the patient's blood to and from the blood treatment apparatus which are different from those in the first relative orientation; and h. at least one of the assemblies' plurality of passageways which establish variable fluid communication with other cavities depending on the relative orientation of the two sides being so configured as to create an unobstructed fluid path from the first blood treatment apparatus fluid fitting to the second blood treatment apparatus fluid fitting such that flow through the blood treatment portion of the entire blood circuit is uninterrupted during a transition from a first of the at least two relative orientations of the two sides to a second of the at least two relative orientations of the two sides and in all of the at least two relative orientations other than the first and second and simultaneously fluid flow between the two patient fluid fittings is prevented in all of the at least two relative orientations.

* * * * *